(12) United States Patent
Huang et al.

(10) Patent No.: US 12,249,891 B2
(45) Date of Patent: Mar. 11, 2025

(54) MOTOR

(71) Applicant: Nidec Corporation, Kyoto (JP)

(72) Inventors: Ting Huang, Dalian (CN); Zhipeng Li, Dalian (CN); Wang Xiaoge, Dalian (CN)

(73) Assignee: NIDEC CORPORATION, Kyoto (JP)

( * ) Notice: Subject to any disclaimer, the term of this patent is extended or adjusted under 35 U.S.C. 154(b) by 164 days.

(21) Appl. No.: 17/954,382

(22) Filed: Sep. 28, 2022

(65) Prior Publication Data

US 2023/0101359 A1   Mar. 30, 2023

(51) Int. Cl.
| | |
|---|---|
| *H02K 5/16* | (2006.01) |
| *A61P 25/28* | (2006.01) |
| *C07K 7/06* | (2006.01) |
| *H02K 5/15* | (2006.01) |
| *A61K 38/00* | (2006.01) |

(52) U.S. Cl.
CPC .............. *H02K 5/16* (2013.01); *A61P 25/28* (2018.01); *C07K 7/06* (2013.01); *H02K 5/15* (2013.01); *A61K 38/00* (2013.01)

(58) Field of Classification Search
CPC ... H02K 5/15; H02K 5/16; H02K 5/18; A61P 25/28; C07K 7/06; A61K 38/00
USPC ..................................... 310/400–401, 90–91
See application file for complete search history.

(56) References Cited

U.S. PATENT DOCUMENTS

| | | | | |
|---|---|---|---|---|
| 2,043,655 | A * | 6/1936 | Ehrmann | H02K 9/14 |
| | | | | 310/57 |
| 3,238,401 | A * | 3/1966 | Baclawski | H02K 5/04 |
| | | | | 310/91 |
| 4,384,224 | A * | 5/1983 | Spitler | H02K 5/161 |
| | | | | 310/58 |
| 4,557,041 | A * | 12/1985 | White | H02K 5/15 |
| | | | | 310/410 |
| 5,949,163 | A * | 9/1999 | Karafillis | H02K 5/24 |
| | | | | 310/51 |
| 8,502,436 | B2 * | 8/2013 | Wilson, Jr. | H02K 5/207 |
| | | | | 310/90 |
| 10,491,060 | B2 * | 11/2019 | Wang | H02K 21/22 |
| 2019/0084407 | A1 * | 3/2019 | Takemoto | H02K 5/15 |

FOREIGN PATENT DOCUMENTS

JP         2013-158204 A       8/2013

* cited by examiner

*Primary Examiner* — Burton S Mullins
(74) *Attorney, Agent, or Firm* — Keating & Bennett, LLP

(57) ABSTRACT

A motor includes a casing including a wall portion and a bottom portion on an outside of the wall portion in an axial direction. The bottom portion includes a bearing holding portion in a center region of the bottom portion, and a base portion between the wall portion and the bearing holding portion. The base portion includes a plate-shaped portion and a protrusion portion in the plate-shaped portion. The protrusion portion includes a first protrusion portion protruding from an outer surface on an outside of the plate-shaped portion in the axial direction toward an outside of the casing in the axial direction, and a second protrusion portion protruding from an inner surface of the plate-shaped portion in the axial direction toward an inside of the casing. The first protrusion portion and the second protrusion portion oppose each other.

10 Claims, 3 Drawing Sheets

MOTOR

CROSS REFERENCE TO RELATED APPLICATION

The present application claims priority under 35 U.S.C. § 119 to CN patent application No. 202111159425, filed on Sep. 30, 2021, the entire contents of which are hereby incorporated herein by reference.

1. Field of the Disclosure

The present disclosure relates to a motor.

2. Background

Conventionally, a motor of the related art has a casing. The motor is connected to a product of a customer via a bottom portion of the casing. In this case, the bottom portion of the casing is cut to ensure sealability with the product of the customer.

When further sealing is required, the bottom portion of the casing and the product of the customer are fixed with bolts or the like.

The introduction related to the above technical background is described to clearly and fully describe the technical solutions of the present disclosure and to facilitate understanding of those skilled in the art, and it should not be considered that the present disclosure and the above technical solutions are known to those skilled in the art.

In the motor of the related art, since the entire outer surface of the bottom portion of the casing needs to be cut, it is necessary to secure a thickness of the bottom portion in order to secure processing strength. Thus, a weight of the casing increases, and material cost increases. A cutting area is large, a long processing time is required, and processing cost is high.

SUMMARY

A motor according to an example embodiment of the present disclosure includes a casing. The casing includes a wall portion and a bottom portion provided on an outside of the wall portion in an axial direction. The bottom portion includes a bearing holding portion positioned in a center region of the bottom portion and a base portion provided between the wall portion and the bearing holding portion. The base portion includes a plate-shaped portion and a protrusion portion provided in the plate-shaped portion. The protrusion portion includes a first protrusion portion protruding from an outer surface on an outside of the plate-shaped portion in the axial direction toward an outside of the casing in the axial direction, and a second protrusion portion protruding from an inner surface on an inside of the plate-shaped portion in the axial direction toward an inside of the casing in the axial direction. The first protrusion portion and the second protrusion portion oppose each other in the axial direction.

The above and other elements, features, steps, characteristics and advantages of the present disclosure will become more apparent from the following detailed description of the example embodiments with reference to the attached drawings.

DETAILED DESCRIPTION

The foregoing and other features of the present disclosure will be described with reference to the drawings and the following specification. In the specification and the drawings, although specific example embodiments of the present disclosure are specifically described, some example embodiments in which the present disclosure can be adopted are merely clarified. The present disclosure is not limited to the described example embodiments, but includes all changes, modifications, and equivalents falling within the scope of the appended claims.

In the description of example embodiments of the present disclosure, the term "and/or" includes any one and all combinations of one or a plurality of associated listed terms. The terms "including (inclusion)", "having", and the like refer to the presence of stated features, elements, components, or assemblies, but do not exclude the presence or addition of one or a plurality of other features, elements, components, or assemblies.

In the description of example embodiments of the present disclosure, the terms "one", "the", and the like in a singular form may include plural forms, and should be understood in a broad sense as "one kind", and is not limited to the meaning of "one". The term "the" should be understood as an expression including singular and plural forms, unless clearly specified otherwise in the preceding and following sentences. The expressions "based on", "according to", and "in accordance with" should be understood as "based on at least a part . . . ".

In the following description of example embodiments of the present disclosure, for the sake of convenience in description, a direction extending along a central axis OO' of a motor 10 or a direction parallel thereto is referred to as an "axial direction", and a radial direction about the central axis OO' is referred to as a "radial direction". A direction surrounding the central axis OO' is referred to as a "circumferential direction". However, these terms are merely intended to facilitate the description of the example embodiments of the present disclosure, and do not limit actual orientations of a rotor and a motor at the time of use or at the time of manufacture.

Figure 1:
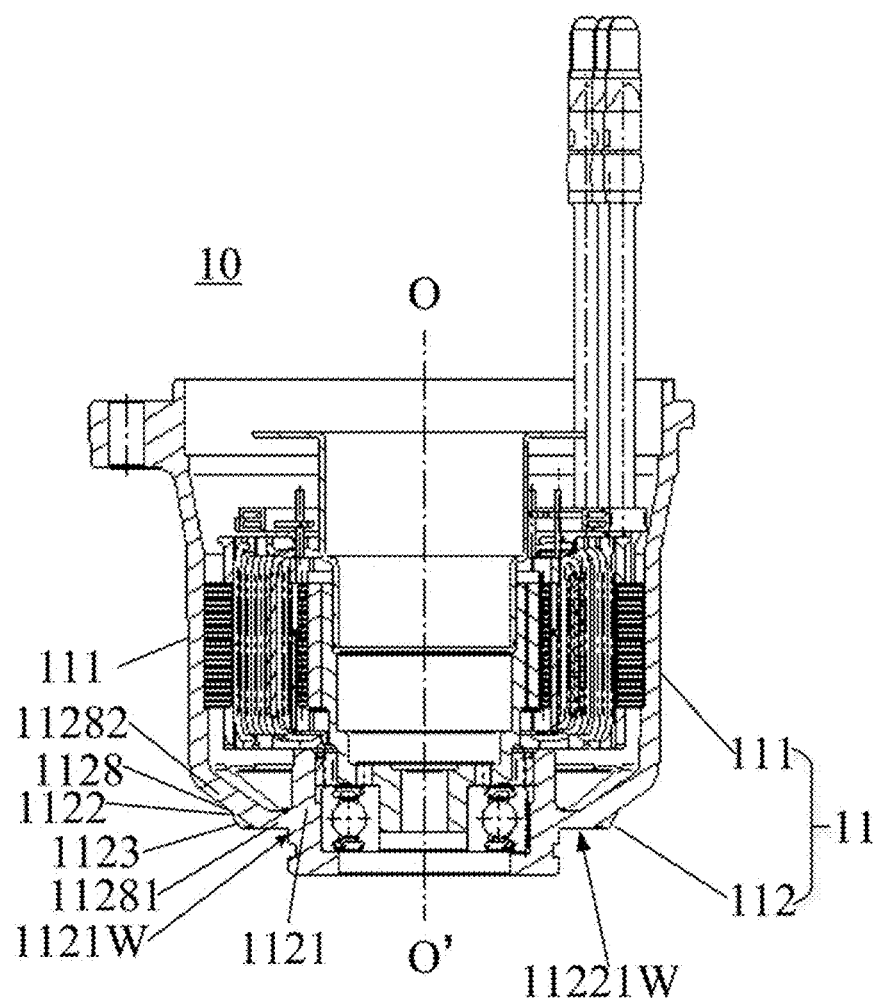
FIG. 1 is a longitudinal sectional view of a motor according to an example embodiment of the present disclosure.
Figure 2:
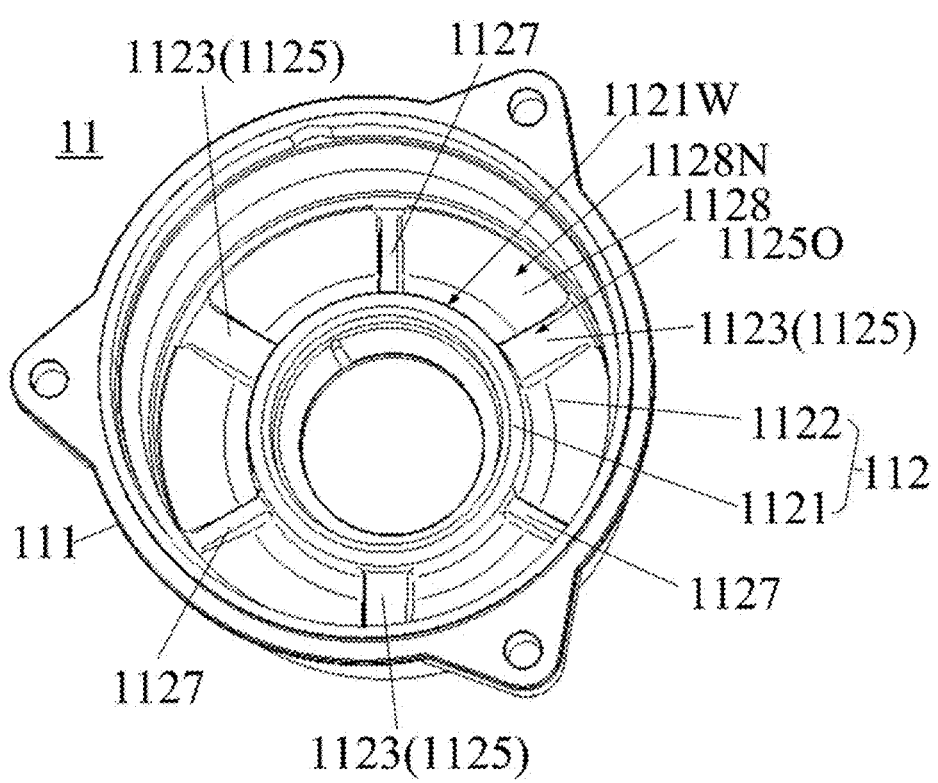
FIG. 2 is a perspective view illustrating an inside of a casing according to an example embodiment of the present disclosure.
Figure 3:
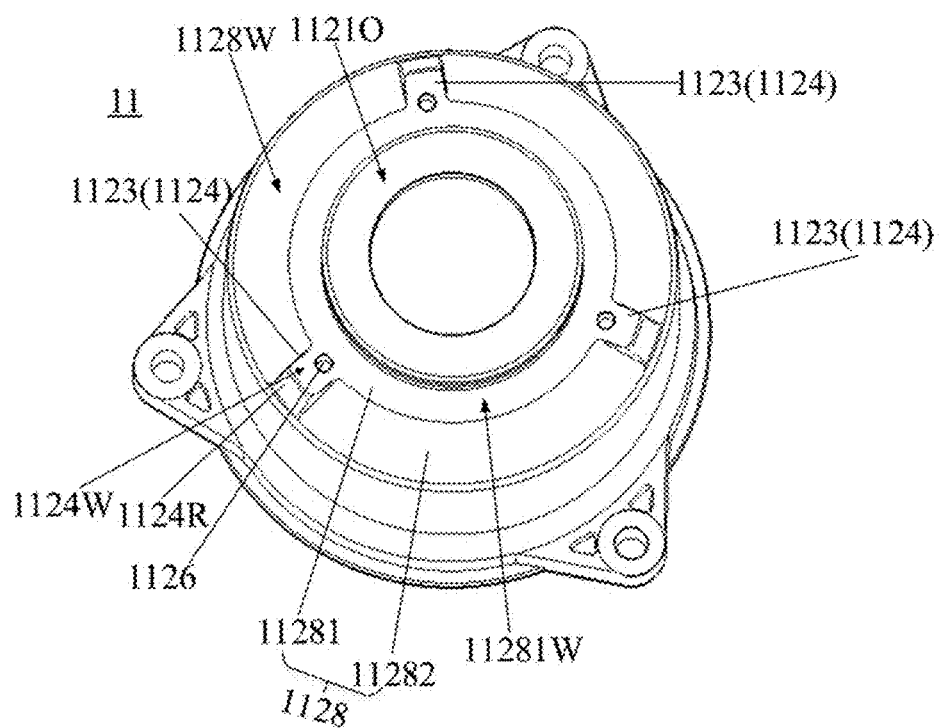
FIG. 3 is a perspective view illustrating an outside of a casing according to an example embodiment of the present disclosure.

Hereinafter, the example embodiments of the present disclosure will be described with reference to the drawings. FIG. 1 is a longitudinal sectional view of a motor 10 according to an example embodiment of the present disclosure taken along a central axis OO' of the motor 10. The central axis OO' of the motor is, for example, a rotation center of a rotation shaft of the motor 10. FIG. 2 is a perspective view of a casing 11 as viewed from an O side, and illustrates an inside of the casing 11 according to the present example embodiment of the present disclosure. FIG. 3 is a perspective view of the casing 11 according to the present example embodiment of the present disclosure as viewed from a O' side, and illustrates an outside of the casing 11.

As illustrated in FIGS. 1 to 3, the casing 11 includes a wall portion 111 and a bottom portion 112 positioned on an outside (O' side) of the wall portion 111 in an axial direction. The wall portion 111 is a cylindrical member. The bottom portion 112 is connected to the wall portion 111. In the present example embodiment, the wall portion 111 and the bottom portion 112 are integrally formed. The bottom portion 112 includes a bearing holding portion 1121 positioned in a center region of the bottom portion 112 and a base portion 1122 provided between the wall portion 111 and the bearing holding portion 1121. The base portion 1122 includes a plate-shaped portion 1128 and a protrusion portion 1123 provided on the plate-shaped portion 1128. The protrusion portion 1123 includes a first protrusion portion 1124 protruding from an outer surface 1128W of the plate-shaped portion 1128 toward the outside of the casing 11, and a second protrusion portion 1125 protruding from an inner surface 1128N of the plate-shaped portion 1128 toward the inside of the casing 11. The first protrusion portion 1124 and the second protrusion portion 1125 face each other in the axial direction. Here, the outside of the casing 11 represents a direction toward the O' side in the axial direction, and the inside of the casing 11 represents a direction toward the O side in the axial direction.

According to the above example embodiment, when connection with a product is performed by using the first protrusion portion 1124 protruding toward the outside from the outer surface 1128W of the plate-shaped portion 1128 of the casing 11, an area of the connection portion is reduced. As a result, flatness of a connection portion is easily grasped, processing becomes easy, and high sealability between the casing 11 and the product can be easily realized. Since a weight of the casing 11 is reduced, cost can be reduced. Strength of the bottom portion 112 of the casing 11 can be increased by the protrusion portion 1123.

In the present example embodiment of the present disclosure, the motor 10 may be of various types. In addition to the casing 11, the motor 10 may further include other components such as a stator, a rotor, and a bearing, and the related art may be referred to.

In the present example embodiment of the present disclosure, the first protrusion portion 1124 and the second protrusion portion 1125 may completely face each other in the axial direction, or may partially face each other. For example, the first protrusion portion 1124 and the second protrusion portion 1125 may completely overlap each other as viewed from the axial direction, and the first protrusion portion 1124 and the second protrusion portion 1125 may partially overlap each other as viewed from the axial direction. For example, a part of the first protrusion portion 1124 and the entire second protrusion portion 1125 may overlap each other in the axial direction, and a part of the second protrusion portion 1125 and the entire first protrusion portion 1124 may overlap each other in the axial direction. The present disclosure is not limited thereto, and may be appropriately changed as necessary.

As illustrated in FIGS. 1 to 3, at least a part of the plate-shaped portion 1128 is an inclined portion 11282. The inclined portion 11282 is a portion inclined with respect to the central axis OO'. The first protrusion portion 1124 protrudes from the outer surface of the inclined portion 11282 toward the outside of the casing 11. The second protrusion portion 1125 protrudes from the inner surface of the inclined portion 11282 toward the inside of the casing 11.

That is, the base portion 1122 includes the inclined portion 11282 having an inclined shape. As a result, the protrusion portion 1123 can be firmly supported, and a space in the casing 11 can be enlarged.

In the present example embodiment of the present disclosure, the plate-shaped portion 1128 is provided between the bearing holding portion 1121 and the wall portion 111.

Thus, the inclined portion 11282 is also provided between the bearing holding portion 1121 and the wall portion 111. The inclined portion 11282 may be any portion of the plate-shaped portion 1128. For example, the entire plate-shaped portion 1128 may be the inclined portion 11282. For example, like a case where a portion of the plate-shaped portion 1128 on the wall portion 111 side may be the inclined portion 11282 or a portion of the plate-shaped portion 1128 on the bearing holding portion 1121 side may be the inclined portion 11282, the inclined portion may be appropriately changed as necessary.

As illustrated in FIGS. 1 and 3, the plate-shaped portion 1128 may further include a horizontal extension portion 11281. The horizontal extension portion 11281 extends from an outer peripheral surface 1121W of the bearing holding portion 1121 in the radial direction toward the inclined portion 11282. An end surface 11281W on an outside of the horizontal extension portion 11281 in the axial direction is a smooth surface, and the inclined portion 11282 is provided between the horizontal extension portion 11281 and the wall portion 111.

As a result, the area of the connection portion can be increased, and the sealability can be further improved. In the present example embodiment, it is not necessary to cut at least an end surface on an outside of the inclined portion 11282 in the axial direction as compared with a case where it is necessary to cut the entire outer surface of the entire bottom portion 112 of the casing 11 in order to form a smooth surface. Accordingly, processing cost can be reduced.

As illustrated in FIG. 3, although the end surface 11281W on an outside of the horizontal extension portion 11281 in the axial direction and an end surface 1124W on an outside of the first protrusion portion 1124 in the axial direction are flush with each other, the present disclosure is not limited thereto. For example, the end surface 11281W on the outside of the horizontal extension portion 11281 in the axial direction and the end surface 1124W on the outside of the first protrusion portion 1124 in the axial direction may not be flush with each other, and may be confirmed in accordance with a specific shape of a corresponding portion of the product connected to the casing 11. That is, the end surface 11281W on the outside of the horizontal extension portion 11281 in the axial direction and the end surface 1124W on the outside of the first protrusion portion 1124 in the axial direction can be connected to the product.

As illustrated in FIG. 3, the horizontal extension portion 11281 has an annular shape, but is not limited thereto, and the horizontal extension portion 11281 may have other shapes.

The plate-shaped portion 1128 may not include the horizontal extension portion 11281 but may include only the inclined portion 11282. That is, the inclined portion 11282 may extend from the outer peripheral surface 1121W of the bearing holding portion 1121 in the radial direction to the wall portion 111, and may be appropriately changed as necessary. The entire plate-shaped portion 1128 may have a horizontal plate shape, and the first protrusion portion 1124 and the second protrusion portion 1125 may protrude from the outer surface and the inner surface of the horizontal plate-shaped portion 1128, respectively. A specific shape of the plate-shaped portion 1128 may be appropriately changed as necessary.

As illustrated in FIG. 3, a hole portion 1126 is provide din the protrusion portion 1123. The hole portion 1126 is recessed from a part of the outer surface of the first protrusion portion 1124 toward an inside of the motor 10. Here, the inside of the motor 10 is a direction facing the O side in the axial direction.

As a result, the casing 11 and the product can be fixed via the hole portion 1126 by using a fixing component such as a bolt. Here, the hole portion 1126 is provided in the protrusion portion 1123, and thus, it is possible to more firmly fix the casing by guaranteeing the strength of the casing 11 at the time of fixing by using the fixing component.

As illustrated in FIG. 2, the hole portion 1126 does not penetrate through the protrusion portion 1123 in the axial direction. That is, the hole portion 1126 does not penetrate an end surface 1125O of the second protrusion portion 1125 on the O side. As a result, interference between the fixing component such as the bolt and a motor internal component can be prevented. The present disclosure is not limited thereto, and the hole portion 1126 may penetrate the protrusion portion 1123 in the axial direction.

A plurality of protrusion portions 1123 may be arranged along the circumferential direction, and may include, for example, three protrusion portions 1123 as illustrated in FIGS. 2 and 3. Meanwhile, the number of protrusion portions 1123 is not limited thereto, and may be two or may be more than three. The plurality of protrusion portions 1123 arranged along the circumferential direction may be arranged at equal intervals or not at equal intervals in the circumferential direction.

In FIG. 2, a rib portion 1127 is provided between two adjacent protrusion portions 1123. A dimension of the rib portion 1127 in the circumferential direction is smaller than a dimension of the protrusion portion 1123 in the circumferential direction. As a result, the strength of the casing 11 can be further enhanced by the rib portion 1127. The dimension of the rib portion 1127 in the circumferential direction is smaller than the dimension of the protrusion portion 1123 in the circumferential direction, and the weight of the casing 11 can be reduced. The present disclosure is not limited thereto, and for example, the dimension of the rib portion 1127 in the circumferential direction may be equal to or larger than the dimension of the protrusion portion 1123 in the circumferential direction.

As illustrated in FIG. 2, both the protrusion portion 1123 and the rib portion 1127 are rectangular as viewed from the axial direction. More specifically, each of an outer shape of the protrusion portion 1123 and an outer shape of the rib portion 1127 is rectangular as viewed from the axial direction. As a result, since the shapes of the protrusion portion 1123 and the rib portion 1127 are simplified, the molding of the casing 11 becomes easy. The outer shapes of the protrusion portion 1123 and the rib portion 1127 are not limited to the above shapes, and may be, for example, other shapes such as a triangular shape, a circular shape, a polygonal shape, or an irregular shape as viewed from the axial direction.

As illustrated in FIG. 2, the rib portion 1127 protrudes from the inner surface 1128N of the plate-shaped portion 1128 toward the inside of the casing 11 (0 side in the axial direction). That is, the rib portion 1127 is provided only on the inner surface 1128N of the plate-shaped portion 1128. As a result, the weight of the casing 11 can be reduced. The present disclosure is not limited thereto, and for example, the rib portion 1127 may protrude from the outer surface 1128W (see FIG. 3) of the plate-shaped portion 1128. As a result, the strength of the casing 11 can be further increased. In this case, a height in the axial direction protruding from the outer surface 1128W is equal to or less than a height of the first protrusion portion 1124 in the axial direction.

As illustrated in FIGS. 1 and 2, the protrusion portion 1123 extends from the wall portion 111 of the casing 11 to the outer peripheral surface 1121W of the bearing holding portion 1121 in the radial direction. As a result, the support strength of the bearing holding portion 1121 can be increased. The present disclosure is not limited thereto, and a position of the protrusion portion 1123 in the radial direction may be other positions. For example, an outer end of the protrusion portion 1123 in the radial direction may not be connected to the wall portion 111 of the casing 11. As illustrated in FIG. 2, an inner end of the protrusion portion 1123 in the radial direction is connected to the outer peripheral surface 1121W of the bearing holding portion 1121, but may not be connected thereto.

As illustrated in FIGS. 1 and 3, the plate-shaped portion 1128 includes the horizontal extension portion 11281, and the first protrusion portion 1124 extends from the outer peripheral surface of the horizontal extension portion 11281 to the wall portion 111 of the casing 11 in the radial direction. The present disclosure is not limited thereto, and the first protrusion portion 1124 may extend, for example, from the outer peripheral surface 1121W of the bearing holding portion 1121 to the wall portion 111 of the casing 11 in the radial direction. That is, the first protrusion portion 1124 may protrude from the outer end surface 11281W of the horizontal extension portion 11281 toward the outside of the casing 11 (O' side in the axial direction).

In the present example embodiment, the end surface 1124W on the outside of the first protrusion portion 1124 in the axial direction is a smooth surface. As a result, the casing 11 and the product can be well sealed and accurately positioned. It is not necessary to cut the entire outer surface of the bottom portion 112 of the casing 11, and since only the end surface of the first protrusion portion 1124 on the O' side in the axial direction may be cut, the processing cost can be further reduced.

As illustrated in FIG. 3, an outer lateral surface 1124R of the first protrusion portion 1124 in the radial direction is the inclined surface. The outer lateral surface 1124R in the radial direction extends toward a center of the casing 11 in the radial direction in a direction from the second protrusion portion 1125 toward the first protrusion portion 1124, that is, in a direction from O to O'. As a result, the casing 11 and the product can be easily attached. The present disclosure is not limited thereto, and the outer lateral surface 1124R of the first protrusion portion 1124 in the radial direction may have another shape such as a surface parallel to the axial direction.

In the present example embodiment, the end surface 1121O on the outside of the bearing holding portion 1121 in the axial direction is a smooth surface. As a result, the casing 11 and the product can be positioned well. The present disclosure is not limited thereto, and the end surface 1121O on the outside of the bearing holding portion 1121 in the axial direction may be a non-smooth surface and may be appropriately changed as necessary.

Although the motors of the present disclosure has been described with reference to the above example embodiments, the above example embodiments may be arbitrarily combined. The present disclosure has been described above merely as an example. That is, the present disclosure is not limited thereto, and appropriate modifications may be made based on the above example embodiments.

According to the example embodiments of the present disclosure, the area of the connection portion is reduced when the first protrusion portion 1124 protruding toward the outside from the outer surface 1128W of the plate-shaped portion 1128 of the casing 11 is used for connection with the product. As a result, the weight of the casing 11 is reduced, and material cost can be reduced. Since the area of the connection portion is reduced, flatness is easily grasped, processing is facilitated, and sealability can be further improved. The strength of the bottom portion 112 of the casing 11 can be increased by the protrusion portion 1123.

Another example embodiment of the present disclosure provides an electrical product including the motor 10 described in the above example embodiments. In the above example embodiments, since a structure of the motor 10 has been described in detail, the description thereof is omitted here.

In another example embodiment of the present disclosure, the electrical product may be any device or equipment using the motor 10 including components in various home appliances, OA equipment, industrial equipment, in-vehicle device, or various kinds of equipment. For example, the electrical product may be a brake system component using the motor 10.

Although the present disclosure has been described above in connection with specific example embodiments, these descriptions are all exemplary and not restrictive of the protection scope of the present disclosure. Those skilled in the art can make various modifications and changes to the present disclosure based on the gist and principle of the present disclosure, and these modifications and changes are also within the scope of the present disclosure.

The example embodiments of the present disclosure have been described above with reference to the drawings. Many features and advantages of the example embodiments have become apparent from the specification. The appended claims are intended to cover all features and advantages described in the gist and specification of the example embodiments. The appended claims are not limited only to the structures and operations exemplified and described in the example embodiments of the present disclosure, but can cover all appropriate changes and equivalents that those skilled in the art can conceive.

Features of the above-described preferred example embodiments and the modifications thereof may be combined appropriately as long as no conflict arises.

While example embodiments of the present disclosure have been described above, it is to be understood that variations and modifications will be apparent to those skilled in the art without departing from the scope and spirit of the present disclosure. The scope of the present disclosure, therefore, is to be determined solely by the following claims.

What is claimed is:

1. A motor comprising:
a stator; and
a casing supporting that stator; wherein
the casing includes a wall portion and a bottom portion provided on an outside of the wall portion in an axial direction;
the bottom portion includes a bearing holding portion positioned in a center region of the bottom portion and a base portion provided between the wall portion and the bearing holding portion;
the base portion includes a plate-shaped portion and a protrusion portion provided in the plate-shaped portion;
the protrusion portion includes a first protrusion portion protruding from an outer surface on an outside of the plate-shaped portion in the axial direction toward an outside of the casing in the axial direction, and a second protrusion portion protruding from an inner surface on an inside of the plate-shaped portion in the axial direction toward an inside of the casing in the axial direction;
the first protrusion portion and the second protrusion portion oppose each other in the axial direction;
all portions of the first protrusion portion and the second protrusion portion are located radially inward from a radially outermost surface of the stator;
a hole portion is in the protrusion portion; and
the hole portion is recessed from a portion of an outer surface of the first protrusion portion toward an inside in the axial direction.

2. The motor according to claim 1, wherein
a plurality of the protrusion portions are arranged along a circumferential direction;
a rib portion is between two adjacent protrusion portions; and
a dimension of the rib portion in the circumferential direction is smaller than a dimension of the protrusion portion in the circumferential direction.

3. The motor according to claim 2, wherein both the protrusion portion and the rib portion are rectangular as viewed from the axial direction.

4. The motor according to claim 2, wherein the rib portion protrudes from the inner surface of the plate-shaped portion toward the inside of the casing.

5. The motor according to claim 1, wherein the protrusion portion extends from the wall portion of the casing up to an outer peripheral surface of the bearing holding portion in a radial direction.

6. The motor according to claim 1, wherein an end surface on the outside of the first protrusion portion in the axial direction is a smooth surface.

7. The motor according to claim 6, wherein
an outer lateral surface of the first protrusion portion in a radial direction is an inclined surface; and
the inclined surface extends toward a center of the casing in the radial direction in a direction from the second protrusion portion toward the first protrusion portion.

8. The motor according to claim 1, wherein
at least a portion of the plate-shaped portion is an inclined portion;
the first protrusion portion and the second protrusion portion protrude from an outer surface on an outside of the inclined portion in the axial direction toward the outside of the casing in the axial direction; and
the second protrusion portion protrudes from an inner surface on an inside of the inclined portion in the axial direction toward the inside of the casing in the axial direction.

9. The motor according to claim 8, wherein
the plate-shaped portion further includes a horizontal extension portion extending from an outer peripheral surface of the bearing holding portion in a radial direction toward the inclined portion;
an end surface on an outside of the horizontal extension portion in the axial direction is a smooth surface; and
the inclined portion is between the horizontal extension portion and the wall portion.

10. An electrical product comprising the motor according to claim 1.

* * * * *

UNITED STATES PATENT AND TRADEMARK OFFICE
CERTIFICATE OF CORRECTION

Page 1 of 1

PATENT NO. : 12,249,891 B2
APPLICATION NO. : 17/954382
DATED : March 11, 2025
INVENTOR(S) : Ting Huang, Zhipeng Li and Wang Xiaoge It is certified that error appears in the above-identified patent and that said Letters Patent is hereby corrected as shown below:

On the Title Page

The Foreign Application Priority Data (30) should be included as follows:
Sept. 30, 2021 (CN) .............202111159424.9

Signed and Sealed this
Fifteenth Day of April, 2025

Coke Morgan Stewart
*Acting Director of the United States Patent and Trademark Office*